United States Patent [19]

Fellows

[11] Patent Number: 6,078,042

[45] Date of Patent: Jun. 20, 2000

[54] CALIBRATION STANDARD FOR INFRARED ABSORPTION GAUGE

[75] Inventor: Timothy Gordon Fellows, Cirencester, United Kingdom

[73] Assignee: Infrared Engineering Limited, Maldon Essex, United Kingdom

[21] Appl. No.: 09/029,242

[22] PCT Filed: Sep. 5, 1996

[86] PCT No.: PCT/GB96/02182

§ 371 Date: Mar. 4, 1998

§ 102(e) Date: Mar. 4, 1998

[87] PCT Pub. No.: WO97/09605

PCT Pub. Date: Mar. 13, 1997

[30] Foreign Application Priority Data

Sep. 5, 1995 [GB] United Kingdom .................... 9518100

[51] Int. Cl.[7] .................................................. G01D 18/00
[52] U.S. Cl. ......................................................... 250/252.1
[58] Field of Search ........................ 250/252.1; 359/350, 359/359; 252/587; 73/1.01 T

[56] References Cited

U.S. PATENT DOCUMENTS

| | | |
|---|---|---|
| 3,478,210 | 11/1969 | Janacek . |
| 4,082,950 | 4/1978 | Chen . |
| 4,465,929 | 8/1984 | Edgar .................................. 250/252.1 |
| 4,832,448 | 5/1989 | Jones ....................................... 350/166 |

FOREIGN PATENT DOCUMENTS

| | | |
|---|---|---|
| 0098075 | 1/1984 | European Pat. Off. . |
| 1055111 | 1/1967 | United Kingdom . |

Primary Examiner—Constantine Hannaher
Attorney, Agent, or Firm—Miles & Stockbridge, P.C.; William L. Feeney

[57] ABSTRACT

A calibration standard for use with an infrared optical absorption measurement gauge having an assembly with an optical interference filter (22) and one or more optical elements. The interference filter has spectrally selective properties so that all but a selected spectral band is reflected by the filter towards the detectors of the gauge. The transmitted band is selectively absorbed by the optical element(s) which are spectrally unselective and also directed towards the detectors of the gauge. The position and strength of the selected band can thereby be adjusted to simulate an absorption spectrum, i.e., a corresponding spectral band which is characteristic of the absorption spectrum of a material under measurement. The standard is used to calibrate the absorption measurement gauge.

11 Claims, 6 Drawing Sheets

CALIBRATION STANDARD FOR INFRARED ABSORPTION GAUGE

This invention relates to a calibration standard for an infrared (IR) absorption gauge. The standard may be used to calibrate such a gauge during measurement of some quantity or parameter. For example, quantities such as moisture content, fat and protein content of foodstuffs, sorbed amounts of substances, thicknesses of coatings or films can be measured; or parameters, such as the degree of cure of resins, may be determined by the gauge. The gauge will need to be calibrated periodically to ensure that accurate measurements or determinations are made and this is where the standard is used.

IR absorption gauges operate by projecting infrared radiation, at two or more wavelengths, onto a sample of material and measuring the amount of radiation reflected, transmitted, or scattered by the sample. Signals, proportional to the measured amounts, are processed to determine the required quantities or parameters. For example, moisture content can be computed from signals which represent the ratio of the amounts by which two different wavelengths are absorbed by a sample. This technique is well known in the art and requires no further description.

A typical absorption gauge includes (a) a sensing head, which houses an infrared radiation source, optical components and an IR detector, (b) an electronic unit, which may be separate and which provides the necessary computation and display of measurements. Calibration standards according to the invention can be used to check the stability and precision of such a gauge at regular intervals.

U.S. Pat. No. 3,478,210 and U.S. Pat. No. 4,082,950, both describe calibration standards using moisture containing materials, which are viewed through windows, in sealed containers. However, with such standards, there is a problem of effectively sealing the moisture containing materials, in their containers, to prevent degradation with time. Hence, long term stability of these standards, over months or years, is rarely satisfactory.

EP-A-0098075, discloses a calibration standard which employs spectrally selective absorption means for transmitting incident infrared radiation, which is then reflected and diffused before being measured. In particular, anhydrous materials, made of glass containing a rare earth substance, such as didymium glass, provides accurate calibration with good long term stability. However, whilst the latter standard solves the problem of long term stability, the available rare earth substances are useful with only a limited number of IR wavelengths. Moreover, it is difficult to simulate accurately the prominent absorption bands of many substances which need to be measured by IR absorption gauges (for example, substances such as powdered or granulated foodstuffs). Hence, there are limitations on the practical usage of standards, in accordance with EP-0 098 075.

The invention seeks to overcome these limitations by providing a calibration standard including an assembly comprising:
  (i) an optical interference filter having spectrally selective infrared transmission and reflection characteristics, and
  (ii) one or more optical elements, which respectively reflect, transmit, or absorb infrared radiation in a spectrally unselective manner;
    the optical interference filter and the optical element or elements being selected so as to provide, in the assembly, an infrared reflection spectrum having at least one prominent predetermined wavelength absorption band with a predetermined strength.

Compared with the calibration standard of EP-0 998 075, the calibration standard of the invention is an assembly of integers which are selected to produce a required effect. Consequently, the calibration standard of the invention is not limited to a few special wavelengths, because the integers of the assembly can be selected with regard to their type and individual performance characteristics in order to obtain the necessary spectral response. By way of example only, the interference filter could be either an edge filter, or a three cavity peak element with an appropriate narrow bandpass. The other "optical elements" may include a neutral density filter with an appropriate strength, and/or a front coated aluminium mirror. However, these are only examples of how the invention may be put into practice, because other types of interference filter and of the "optical element or elements" may be used to design an assembly with the required infrared reflection spectrum.

Interference filters are well-known and require no detailed description. They are generally employed for example, to obtain light in a narrow wavelength band from a light source having a broader wavelength spectrum. The light that is not transmitted by such filters is reflected and generally no use is made of it. However, according to the present invention, such reflected light is used to form part of the spectrum of light used for calibrating a gauge. The intensity of the light transmitted by the filter is attenuated to a controlled degree and the attenuated light is combined with the light reflected by the filter and directed at the detectors in the gauge; by choosing the wavelength(s) transmitted by the filter and then attenuated to include one or more wavelengths that are absorbed by the sample of interest, the light falling on the gauge detectors can be made to mimic the light directed at the detectors when measuring a sample having a known parameter, i.e. a calibration standard is produced. In other words, the light reaching the gauge detectors is that incident on the filter except in the waveband that is transmitted by the filter, where the intensity of the light is attenuated compared to the reflected light and so the light incident on the detector includes a prominent absorption feature that corresponds to the radiation absorbed by a sample having a known parameter (e.g. moisture content).

By way of example, in the case of measuring moisture content of a sample, a measuring gauge usually relies on measurements made in infrared absorption bands centred on a wavelength of either 1.45 $\mu$m or 1.94 $\mu$m for the water absorbed by the sample, and on a reference wavelength which is not absorbed by the water in the sample. A comparison of the amounts of absorption, in the measurement and reference wavelengths, gives a measure of the moisture content of the sample. In this example, the assembly in the calibration standard could have an IR reflection spectrum with a prominent absorption band centred on 1.94 $\mu$m and having a strength that simulates a corresponding absorption band in a sample having a predetermined (fixed) moisture content.

As the calibration standard of the invention is not limited to special wavelengths, because the integers of the assembly can be selected in order to give an infrared reflection spectrum as close as possible to the infrared absorption spectrum of a sample under measurement, the invention is particularly useful in calibrating measuring gauges used in (e.g.) the tobacco or food industry, where the spectrum of a sample is characteristic of a tobacco, or foodstuff under measurement.

The invention also provides a method of calibrating an infrared absorption gauge, which gauge is arranged to measure the given quantity or parameter of the sample having a characteristic infrared absorption spectrum, the method comprising the steps of:

provided a calibration standard or standards comprising (i) an optical interference filter having spectrally selective infrared transmission and reflection characteristics, and (ii) one or more optical elements which respectively reflect, transmit or absorb infrared radiation in a spectrally unselective manner, selecting the interference filter and said optical elements so that the infrared reflection spectrum of the assembly corresponds substantially to the infrared absorption spectrum of the sample or samples under measurement; and calibrating the absorption gauge with one or more of the said calibration standards.

Embodiments of the invention will now be described with reference to the accompanying drawings, in which.

Figure 6:
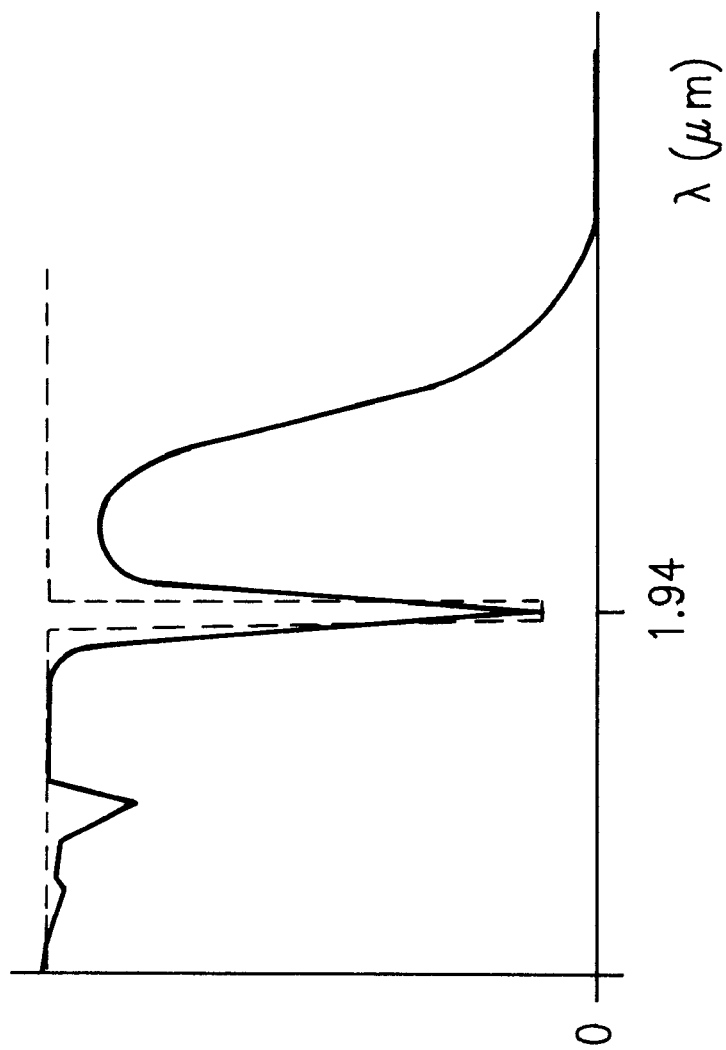
Figure 7:
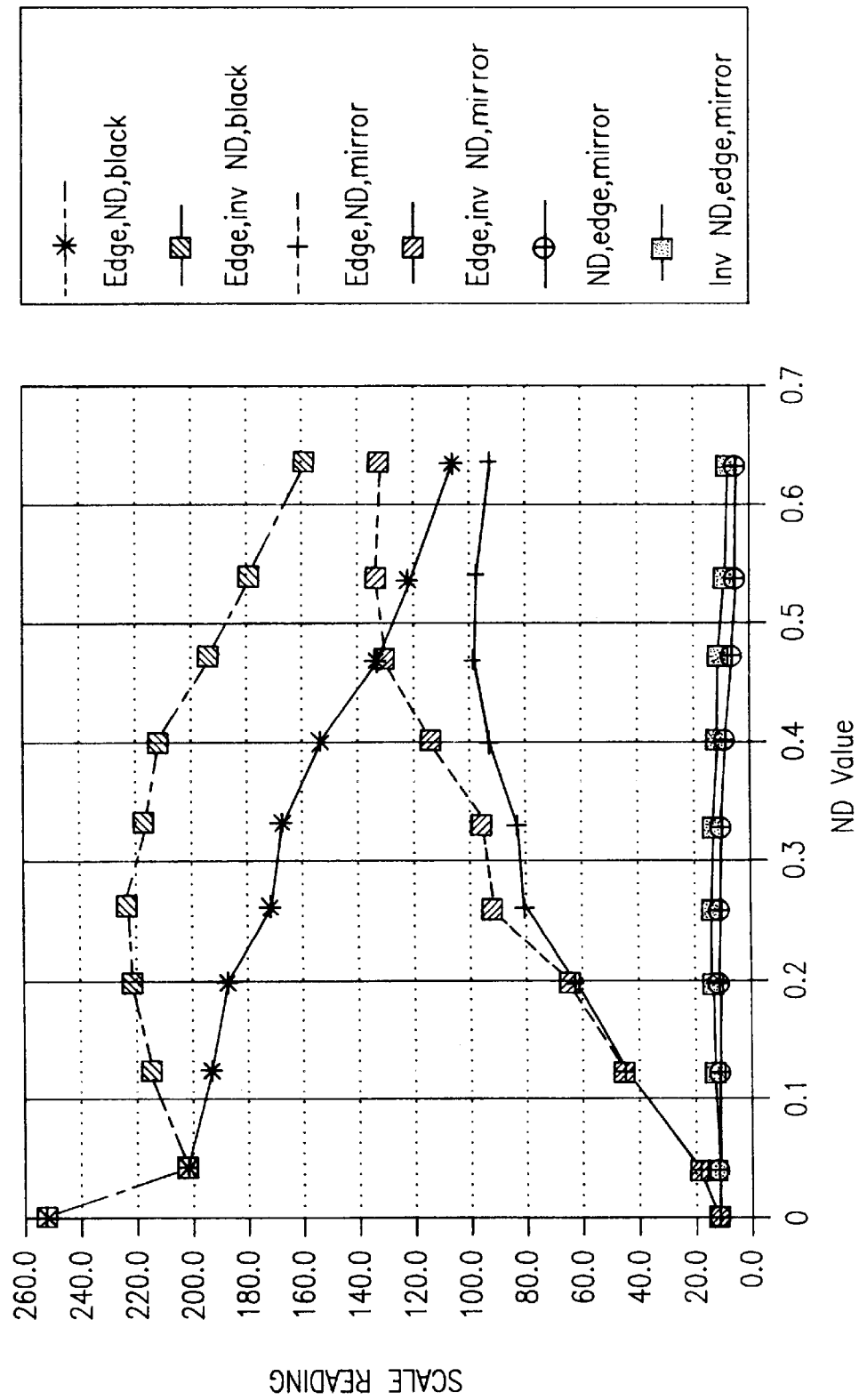
Figure 8:
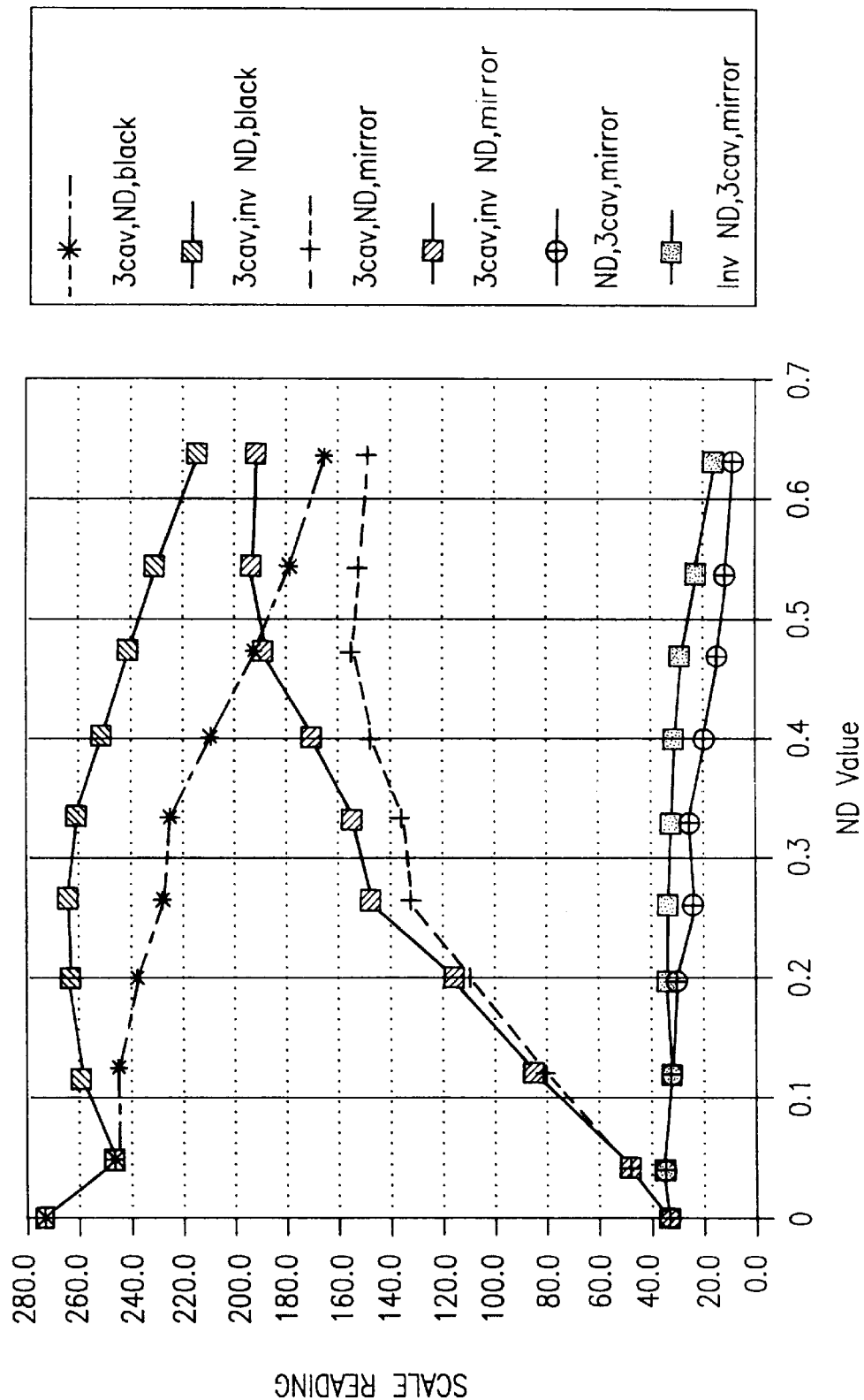

FIG. 6 is a graph on which is superimposed a transmission spectrum of water and a reflection spectrum of assembly 6 in the calibration standard of the preferred embodiment of the invention; and FIGS. 7 and 8 are graphs for use in selecting ND filters in assembly 6.

With reference to the drawings, a calibration standard 1, according to an embodiment of the invention, is attached to a sensing head 2 of an infrared absorption gauge. The construction and operation of the gauge will be known to those skilled in the art so no detailed description will be given. The standard 1 is shown attached to the head 2 during a calibration mode. Normally, the standard 1 is removed so that the gauge can sense material 7 passing beneath head 2. During such a measurement mode, the actual path taken by measurement infrared radiation beams 3 is shown by the broken lines, which show a reflection of these beams from the surface of material 7 back into the gauge. Some of the incident infrared energy (3) will be absorbed by the material 7, the amount of this absorption representing the property to be determined (such as the moisture content of a paper web).

Figure 1:
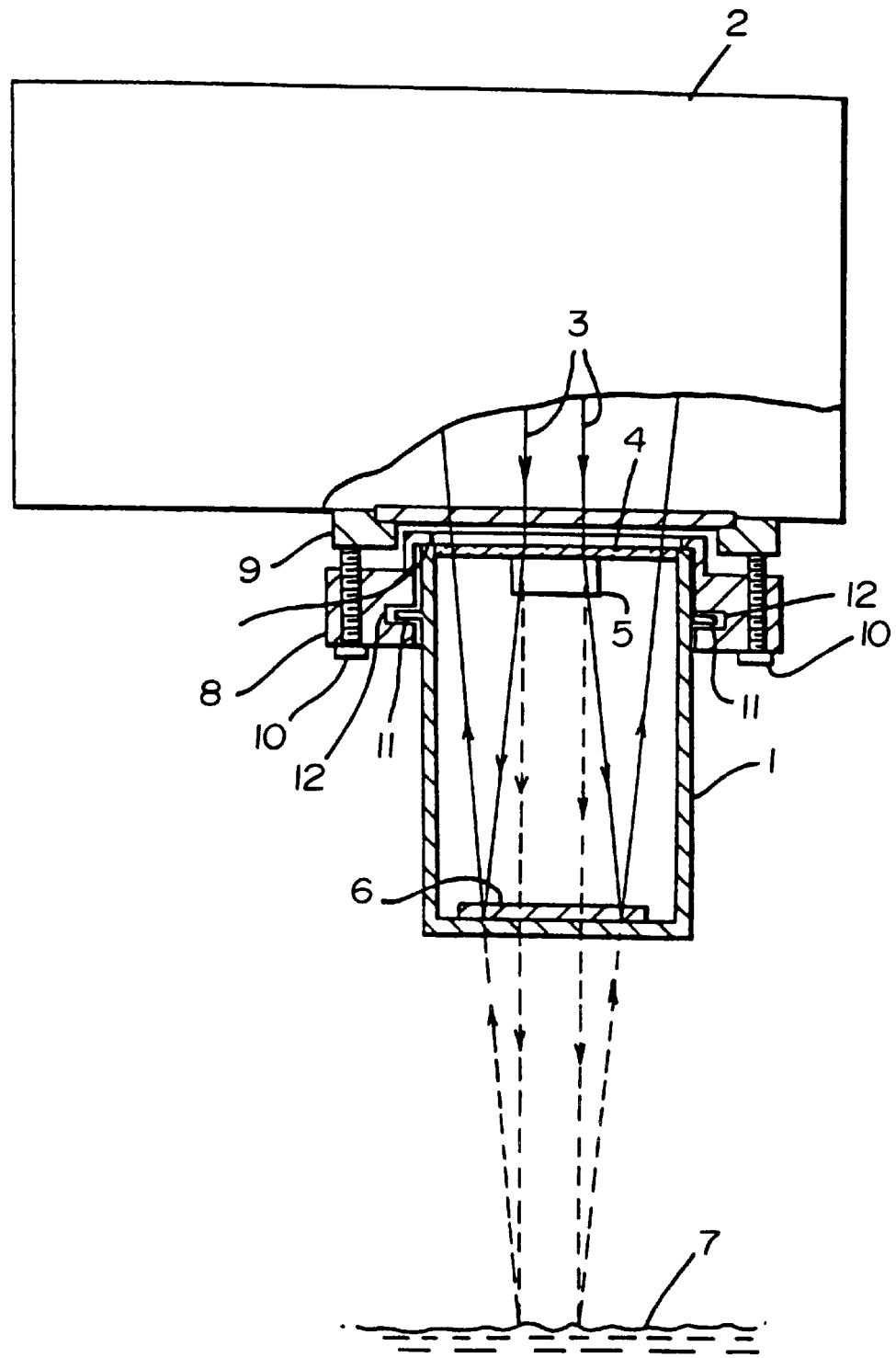
FIG. 1 is a side elevation, partly in section, illustrating a calibration standard according to one embodiment of the invention.

With calibration standard 1 fitted to head 2 (as shown in FIG. 1) incident infrared radiation beams 3 first pass through an IR transmissive window 4, then through a diffuser 5 before passing through a filter assembly 6. Diffuser 5 diminishes the intensity of beams 3, but increases their divergence. Filter assembly 6 exhibits a reflection spectrum corresponding with the infrared absorption spectrum of the material 7 which is being measured (this is explained in more detail below).

By way of example, material 7 is a web of paper moving continuously through a sample zone of sensing head 2, the web having a variable quantity of water sorbed onto it.

As mentioned above, when the calibration standard 1 is removed from head 2, beams 3 follow the path shown by the broken lines. The infrared radiation reflected from the surface of material 7 entering the head 2 lacks components which have been absorbed by material 7 (in particular, absorbed by the water in the paper web). The absorption spectrum of water is shown in FIG. 6 where two characteristic troughs occur due to absorption bands of water at 1.45 and 1.94 $\mu$m, the latter absorption band being the more prominent. As explained in more detail in EP-A-0098075 components 5 and 6 of the calibration standard 1 are arranged so that the path of infrared radiation reflected from component 6 (shown by continuous lines) is the same as the path which would be followed by the radiation reflected from the material 7 in the absence of the standard 1. In other words, component 6 would produce a virtual image of component 5 in a plane coincident with the surface material 7. In this particular case, the optical arrangement is such that component 6 is located at about one half of the distance between the region or exit from which the measurement beams emerge from the sensing head 2 and the surface of the material 7 being measured. Beams of radiation will therefore take the same path and interact identically with the components 5, 6 and with optical components and an IR detector or photocell assembly in head 2. The optical arrangement may be considered as one in which diffused radiation (from component 5) is returned (by component 6) to window 4 at circularly symmetric angles of incidence substantially similar to corresponding angles of incidence of IR radiation which would be reflected from the material 7 at a given sample distance from the sensing head 2 of the infrared absorption gauge. This greatly improves the performance of the calibration standard compared with prior art calibration standards, because detectors (e.g. photocells) used in head 2 commonly exhibit a non-uniform sensitivity and a non-uniform spectral response over their surface.

As explained in more detail in EP-A-0 098 075 in order to achieve the necessary coincidence of paths of the beams of radiation re-entering the sensing head 2 from either the calibration standard 1, or material 7, the optical assembly 6 must be set at a normal angle to the mean direction in which the radiation beams 3 emerge from the sensing head 2. As errors in optical alignment and production tolerances lead to some variation in the direction of emerging beams 3 from one sensing head to another, provision is made to adjust the angle at which the calibration standard 1 is mounted on the sensing head 2. An example of such an adjustable mounting shown by reference numbers 8 to 12 is described in EP-A-0 098 075.

Figure 2:
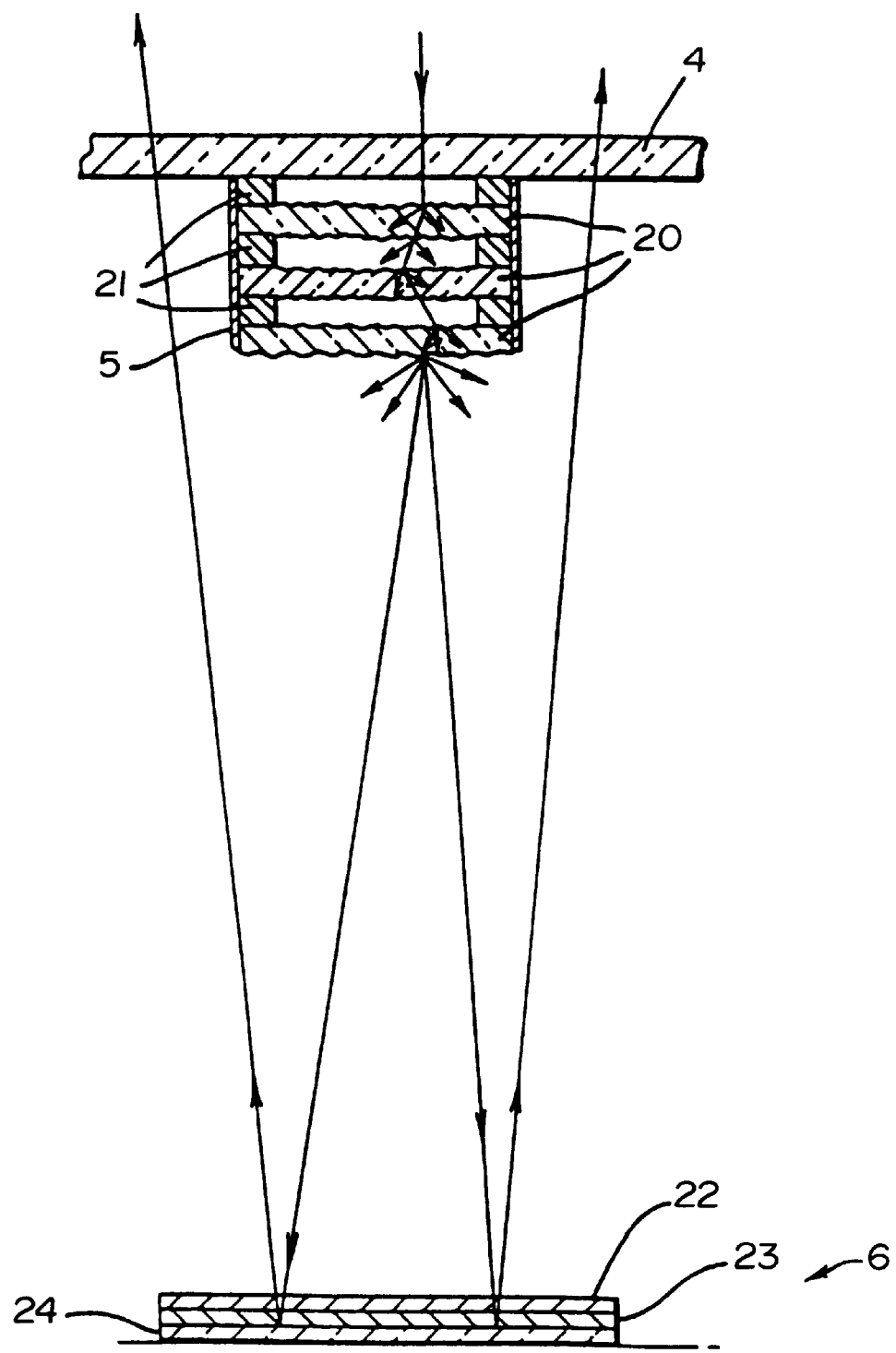
FIG. 2 is a sectional elevation through components 5 and 6 of the calibration standard shown in FIG. 1.

FIG. 2 shows the sub-assemblies 5 and 6 in greater detail. Sub-assembly 5 comprises three circular discs 20, which are separated by annular spacer rings 21. Discs 20 are made of a material that is transparent in the spectral operating range of the infrared absorption gauge and has both of its major faces ground. Grinding of the major surfaces of transparent materials, such as glass, produces a relatively limited range of angles of scattered light. Hence, it is sometimes necessary, as in this example, to use a number of ground discs to produce sufficient diffusion. Alternatively, a material may be used for making the discs which is translucent and which scatters light throughout its thickness, rather than just at the surface. In such a case, multiple discs would not be necessary.

Spacers 21 improve the diffusion efficiency and lead to a divergent beam of radiation, which is more uniform over its surface.

Sub-assembly 6 is an assembly in accordance with one embodiment of the invention. The assembly essentially reflects the incident beams back into the head so that the infrared reflection spectrum corresponds, as near as possible, to the infrared absorption spectrum of the sample 7 which is normally being measured. Sub-assembly 6 comprises an optical interference filter 22 having spectrally selective infrared transmission and reflection characteristics; a neutral density filter 23 which both reflects and transmits light of wavelengths passing through the interference filter 22; and a mirror 24 which returns the wavelengths passing through the neutral density filter back to the interference filter 22. The neutral density filter 23 and mirror 24 are spectrally unselective to the infrared radiation, so that they do not introduce any spectrally prominent feature (as in the case of the interference filter—which is, in comparison, spectrally selective).

Figure 4:
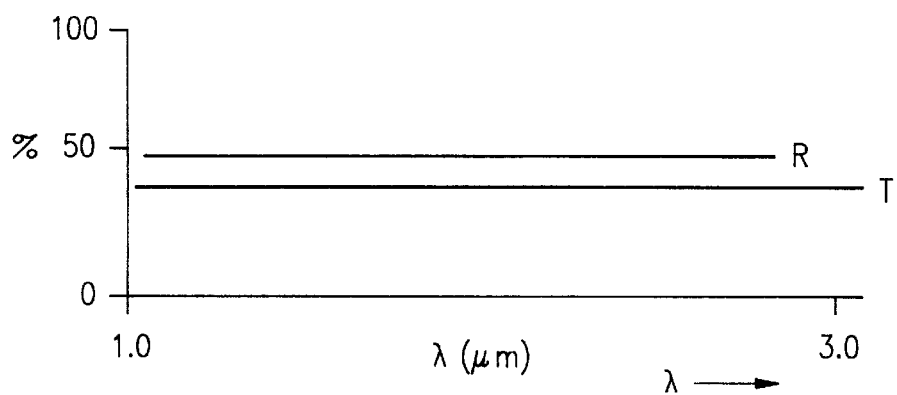
FIG. 4 is a graph showing transmission and reflection of neutral density filter over the same wavelength range, the neutral density filter being another integer of assembly 6.
Figure 5:
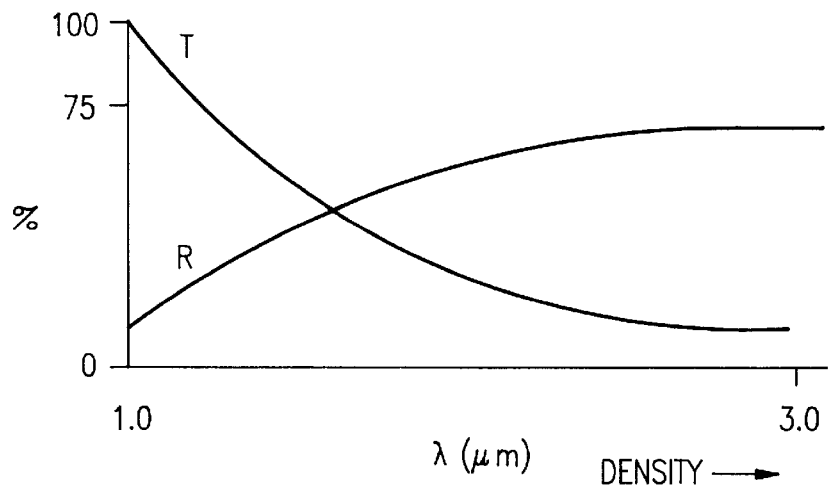
FIG. 5 is a similar graph to FIG. 4 except for showing a neutral density filter having a variable transmission/reflection characteristic over the wavelength range.

The principle of operation of the sub-assembly 6 is as follows. The diffused beams of infrared radiation passing through sub-assembly 5 have a range of wavelengths, most of which are blocked by interference filter 22 and hence reflected. Filter 22 is therefore used in a "reflection mode", whereby some wavelengths are reflected back from sub-assembly 6 into the sensing head 2. However, the wavelengths which pass through the interference filter 22 are intercepted by neutral density filter 23. Neutral density filters are used in transmission to attenuate a beam of radiation, the word "neutral" implying a constant attenuation factor over a spectral range. This is illustrated, in FIG. 4 by the transmission response extending parallel to the wavelengths axis. The neutral density filter 23, as used in the invention, is also capable of partially reflecting incident radiation and the word "neutral" again implies a constant attenuation factor over the spectral range. This is similarly illustrated in FIG. 4 by the reflection characteristics. Some of the incident radiation will also be absorbed by the neutral density filter. Hence, the neutral density (ND) filter will reflect, absorb and transmit respective parts of the incident radiation. For example, a physical ND filter with a density of 0.5 will have a transmission of about 32%, a reflection property of about 25%, and it will absorb the remaining 43% of the incident radiation.

Figure 3:
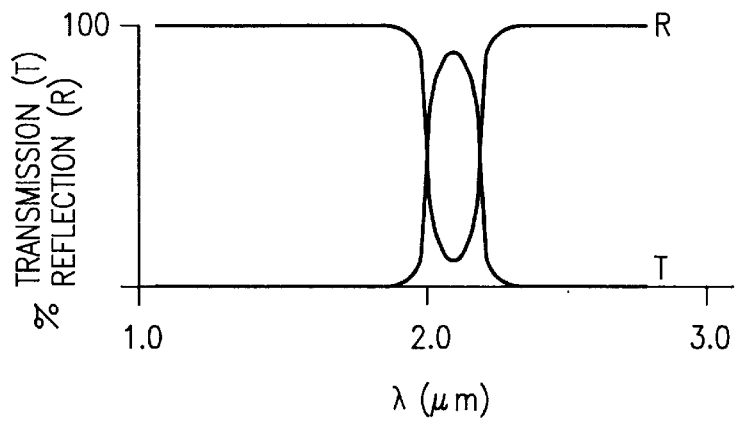
FIG. 3 is a graph showing the percentage transmission and reflection of an interference filter over a wavelength range of about 1.5 to 2.5 $\mu$m, the interference filter being one of the integers of assembly 6.

Assuming now that mirror 24 was not present in the sub-assembly 6, and was replaced by a totally absorbing matt black coating, any of the wavelengths passing through the ND filter 23 would be absorbed and hence not returned through the interference filter. Consequently, the filter response would be as shown in FIG. 3, where a very strong prominent feature is present in the reflection spectrum (ie. the deep trough) and there is a corresponding peak in the transmission spectrum. This strong prominent feature is shown occurring at about 2.1 μm. The depth of the reflection trough (and height of the transmission peak) can be changed by returning some of the radiation which would otherwise be absorbed by the matt black surface. Hence, with the mirror 24 in place, the wavelengths are returned in the preferred waveband, ie. where the prominent feature occurs, giving the effect of more reflection and hence a prominent feature which is not quite as strong as without the mirror 24 in place. In fact, the reflection characteristic without the mirror is considered to be too strong for most calibration applications.

As the density of the ND filter 23 can be controlled, so as to control the amount of reflection and transmission (and absorption), it is also possible to control the amount of light which is reflected from mirror 24 back to the interference filter 22 and hence into the head 2. Thus, by varying the strengths of the ND filter, the amount of light return can be controlled and this enables the strength of the prominent spectral feature (trough depth, or peak height) to be controlled.

Clearly, the construction of the interference filter is such as to produce the prominent spectral feature with the required (narrow) band width centred on the required wavelengths. Hence, the sub-assembly 6 will provide a prominent feature of the required strength as a simulation of the prominent feature appearing in the absorption spectrum of the sample being measured. The absorption spectrum can be determined independently in order to provide the necessary information for constructing sub-assembly 6. Once the sub-assembly has the required spectral response, it can be used for calibration of the gauge for the sample of material in question. If a different material 7 is used, a different calibration standard could be used to calibrate the instrument as before.

The integers of the sub-assembly 6 may be selected in accordance with table 1 shown below. In this table, different combinations of interference filter (IF), neutral density filter (ND), mirror (Refl) and absorber (Abs) are shown together with the strengths of the prominent feature. For example, the first combination of the IF+ND+Refl provides an infrared absorption spectrum of normal strengths. (Clearly, the interference filter is selected to provide the prominent feature, in the spectrum, with the required waveband).

The optical properties of the sub-assembly 6 are preferably as follows:

(a) its spectral transmission and reflection should be relatively uniform (e.g. over its area); and (b) its spectrum should be relatively flat in the region of each of the wavelengths employed by the gauge. Hence either an edge filter or a narrow bandwidth filter with a "flat top" (e.g. a "3 cavity" filter of bandwidth 3–4%) is required. This ensures good temperature stability since the reflectivity of the assembly will not change if the spectra of optical interference filters tend to shift slightly in wavelength as their temperature changes.

TABLE 1

| IF | IF | | ND | | ND | ND |
| ND | ND | IF | IF | IF | IF | IF |
| Refl | Abs | Refl | Refl | Abs | Abs | Refl |
| Normal Absorption | Strong Absorption | Normal Absorption | Weak Absorption | V. Strong Absorption | Strongish Absorption | Weakish Absorption |

It is not necessary to use a neutral density filter, because this could be replaced by another type of filter which is partly reflecting and partly absorbing. For example, a substrate containing either reflective spots on a light absorbing background, or absorptive spots on a reflective background could be used. Combinations based on the use of the latter component (s) are shown in table 2 below.
EQUIVALENTS NOT USING ND

TABLE 2

| { Part Refl / Part Abs Refl } | { Part Refl / (Part Abs) Abs } | IF Refl | { Part Refl / Part Abs } | IF Refl | IF Abs | { Part Refl / Part Abs } | IF Abs | { Part Refl / Part Abs Refl } | { Part Refl / Part Abs } IF |
|---|---|---|---|---|---|---|---|---|---|
| IF | IF | | | | | | | | |

The interference filter 22 may be either an edge filter, or a 3-cavity peak element (approx. 3.5% bandwidth). The neutral density filter (23) is usually less than 0.5 ND units in strength. The mirror 24 is preferably a front-coated aluminium mirror.

The usual order of the elements in the assembly 6 is as shown in FIG. 2. However, there are exceptions to the order of assembly as follows:

(a) Occasionally, the ND filter (23) will need to be in front of the interference filter (22). This is necessary when a very weak calibration check is required (ie. the prominent feature is of low strength).

(b) When a very strong calibration check is required, the mirror 24 will need to be removed, so that the wavelengths of infrared radiation passing through the other elements is absorbed by matt black paint on an end cap in the chamber of the calibration standard 1. However, this is likely to be necessary only for strong moisture calibration checks.

(c) Occasionally, the ND filter 23 will not be required, ie. if the calibration standard gives a correct reading without it. The necessary attenuation in the wavelengths transmitted by the filter is in this case provided by the absorption in the filter itself.

(d) If a 3-cavity filter is used, occasionally an edge filter or a blocking filter (effectively two edge filters) may be required in front of the main interference filter 22, so that the order is edge filter, 3-cavity filter, ND filter, mirror. (See item (5) below).

An edge filter, (short wave pass or long wave pass) should normally transmit infrared light at an absorption wavelength of the gauge, but reflect at least one of the reference wavelengths of the gauge. It should have a relatively flat reflection spectrum over a suitable wavelength range (except, of course, for the prominent feature).

A top hat (3-cavity) filter could be used with a narrow bandwidth (e.g. of around 3.5% bandwidth) which normally transmits at an absorption wavelength, but reflects at the other wavelengths. This should similarly have a relatively flat response.

In constructing assembly 6, the following selection rules preferably apply:

1) Make up a sub-assembly 6 with just a plain mirror 24 and determine the reading with the gauge of interest or another set up in the same way. If this reading is acceptable, no other components need be added to sub-assembly 6. Usually, however, the reading will be too low (i.e. the ratio of the light intensity at the reference wavelength to that at the absorption wavelength is too low), in which case an interference filter which transmits light at at least one of the gauge's absorption wavelengths will be needed. If the plain mirror's reading is too high (which may occur if the material being viewed by the gauge is more absorbing at one of the gauge's reference wavelengths than at the absorption wavelength), an interference filter which transmits light at at least one of the gauge's reference wavelengths will be needed.

2) An edge filter should be incorporated if possible in preference to a 3 cavity filter since it is easier to manufacture with the necessary "flatness" in the appropriate regions of the spectrum.

3) The "edge" of an edge filter needs a gap between two of the wavelengths used by the gauge of at least 10% (e.g. 200 nm at 2000 nm). If no such gap exists, a 3 cavity filter should be used.

4) A 3 cavity filter of bandwidth 3–4% cannot be used if one of the wavelengths being used by the gauge is within 4% of the wavelength which the calibration standard is supposed to be absorbing (e.g. within 80 nm if the absorbed wavelength is 2000 nm). In this case, an edge filter which transmits at both of these. wavelengths is required.

5) If a top hat filter, with centre wavelength x, is chosen and one of the gauge's wavelengths is either less than x/1.2 or greater than x/0.8, this wavelength is likely to coincide with the sidebands of the top hat filter and thermal stability problems will result. These sidebands will need to be blocked off with a blocking (edge) filter which is reflective (i.e. zero transmission) at the wavelength which is causing a problem and transmitting for the other gauge wavelengths. The blocking filter will need to be positioned in front of the main interference filter in the calibration standard.

When a calibration standards needs to be made up to give a specific gauge reading, first a gauge should be set up with the appropriate filter combination and calibration parameters. The sub-assembly 6 should be assembled, without fixing the integers in at this stage, using an initial estimate of the integer configuration and ND strength. To do this, the interference filter, ND filter and mirror, separated by spacer rings, are located in the housing of calibration standard 1. All interference filters (3-cavity, edge or blocking) need to be position so that their coated side is facing the gauge. (The other side shows larger sidebands). If it is not clear which is the coated side, reflectance spectra of the two sides of the filter with a black backing (i.e. instead of a mirror) will show which side has the smaller sidebands.

FIG. 7 shows the typical response (in arbitrary units) of an instrument to calibration standards with difference configurations. If the initial configuration of sub-assembly 6 gives an unsuitable reading, a process of trial and error can be used to determine the correct strength of the ND filter and the correct configuration of the integers, using FIGS. 7 and 8 as a guide. (Note: Although the data in FIGS. 7 and 8 came from an edge and 3-cavity filter, other types of interference filter have been found to show the same characteristics. ND filters give different responses according to whether they are the "normal way up", i.e. with the coating facing the incident light, or inverted. In FIGS. 7 and 8, inverted ND filters are designated as "inv ND" whereas ND filters the normal way up are designated "ND". FIGS. 7 and 8 show that the responses of normal and inverted ND filers is different and this increases the number of choices available to achieve the desired calibration standard.

The sub-assembly can be subjected to a thermal stability test to check its performance under temperature extremes.

Finally, the integers of the sub-assembly should be fixed in place, e,g, by glue.

FIG. 6 shows the kind of match that can be obtained between a transmission spectrum of water and a standard according to an embodiment of the invention. The former spectrum is superimposed on the reflection spectrum of the standard.

I claim:

1. A calibration standard including an assembly comprising:
    (i) an optical interference filter having spectrally selective infrared transmission and reflection characteristics, and
    (ii) one or more optical elements, which respectively reflect, transmit, or absorb infrared radiation transmitted by the optical interference filter in a spectrally unselective manner;
    the optical interference filter and the optical element or elements being selected so as to provide, in the assembly, an infrared reflection spectrum having at least one prominent predetermined wavelength absorption band with a predetermined strength.

2. A standard according to claim 1 in which at least one of the optical elements is a neutral density filter having a predetermined reflection and/or transmission characteristic.

3. A standard according to claim 1 including either a light absorbing, or light reflecting element for absorbing, or reflecting respectively light transmitted by said optical element or elements.

4. A standard according to claim 1 in which said optical element or elements is partly reflecting and partly absorbing.

5. A standard according to claim 4 in which said optical element comprises a substrate containing at least one reflective area and at least one radiation absorbing area.

6. A calibration standard for calibrating an infrared absorption gauge that includes a source of infrared electromagnetic radiation and a detector for detecting the intensity of infrared radiation incident upon it, the standard comprising:
    means for locating the standard relative to an infrared gauge so that it can receive infrared radiation from the radiation source of the gauge and direct infrared radiation towards the detector of the gauge,
    an optical interference filter being locatable to receive infrared radiation from the said radiation source of the gauge, said filter being such that it transmits radiation in at least one infrared wavelength band and reflects radiation having other wavelengths along an optical path on which the gauge detector can be located, and
    optical element means for attenuating the intensity of radiation in at least one wavelength band transmitted by the interference filter and directing the attenuated radiation (if any) along an optical path on which the gauge detector can be located, wherein the interference filter and the optical element means are such that the said radiation directed along said optical path or paths on which the gauge detector can be located has a spectrum made up of said radiation reflected from the filter and said attenuated radiation and so includes at least one prominent predetermined absorption band with a predetermined strength having a wavelength band corresponding to the wavelength band transmitted by the said filter.

7. A standard as claimed in claim 6, wherein the optical element means comprises a neutral density filter having a predetermined reflection and transmission characteristic.

8. A standard as claimed in claim 6, wherein the optical element means comprises at least one optical element that transmits light incident upon it and further includes either a light absorbing, or a light reflecting, element for absorbing or reflecting (respectively) light transmitted by said at least one optical element.

9. A standard as claimed in claim 6, wherein the optical element means comprises at least one element that partly reflect incident radiation.

10. A standard as claimed in claim 9, wherein the said at least one element comprises a substrate containing at least one radiation reflective area and at least one radiation absorbing area.

11. A method of calibrating, or checking the calibration of, an infrared absorption gauge, which gauge is arranged to measure a given quantity or parameter of a sample having a characteristic infrared absorption spectrum, the method comprising the steps of:
    providing a calibration standard or standards comprising (i) an optical interference filter having spectrally selective infrared transmission and reflection characteristics, and (ii) one or more optical elements which respectively reflect, transmit or absorb infrared radiation transmitted by the optical interference filter in a spectrally unselective manner,
    selecting the interference filter and said optical elements so that the infrared reflection spectrum of the assembly corresponds substantially to the infrared absorption spectrum of the sample or samples under measurement; and
    calibrating the absorption gauge with one or more of the said calibration standards.

* * * * *